United States Patent
Roth et al.

(10) Patent No.: US 7,119,093 B2
(45) Date of Patent: Oct. 10, 2006

(54) 3-Z-[1-(4-(N-((4-METHYL-PIPERAZIN-1-YL)-METHYLCARBONYL)-N-METHYL-AMINO)-ANILINO)-1-PHENYL-METHYLENE]-6-METHOXYCARBONYL-2-INDOLINONE-MONOETHANESULPHONATE AND THE USE THEREOF AS A PHARMACEUTICAL COMPOSITION

(75) Inventors: Gerald J. Roth, Biberach (DE); Guenter Linz, Mittelbiberach (DE); Peter Sieger, Mittelbiberach (DE); Werner Rall, Mittelbiberach (DE); Frank Hilberg, Wien (AT); Thomas Bock, Biberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 215 days.

(21) Appl. No.: 10/623,971

(22) Filed: Jul. 21, 2003

(65) Prior Publication Data

US 2004/0176392 A1  Sep. 9, 2004

Related U.S. Application Data

(60) Provisional application No. 60/404,460, filed on Aug. 19, 2002.

(30) Foreign Application Priority Data

Jul. 24, 2002  (DE) ................. 102 33 500

(51) Int. Cl.
*A61K 31/496* (2006.01)
*C07D 403/12* (2006.01)

(52) U.S. Cl. .................. 514/254.09; 544/373
(58) Field of Classification Search ........ 544/373; 514/254.09

See application file for complete search history.

(56) References Cited

U.S. PATENT DOCUMENTS 6,762,180 B1 * 7/2004 Roth et al. ............... 514/228.2

2003/0092756 A1  5/2003  Roth et al.

FOREIGN PATENT DOCUMENTS

| WO | WO 01/27080 A2 | 4/2001 |
|---|---|---|
| WO | WO 01/27081 A1 | 4/2001 |
| WO | WO 02/081445 A1 | 10/2002 |

OTHER PUBLICATIONS

Traxler, Oncologic, vol. 7, p. 215-234 (2003).*
Burke, Stem Cells, vol. 12, p. 1-6 (1994).*

* cited by examiner

*Primary Examiner*—Emily Bernhardt
(74) *Attorney, Agent, or Firm*—Michael P. Morris; Mary-Ellen M. Devlin; Alan R. Stempel

(57) ABSTRACT

The present invention relates to the compound 3-Z-[1-(4-(N-((4-methyl-piperazin-1-yl)-methylcarbonyl)-N-methyl-amino)-anilino)-1-phenyl-methylene]-6-methoxycabonyl-2-indolinone-monoethanesulphonate of formula I and the use thereof as a pharmaceutical composition Formula I:

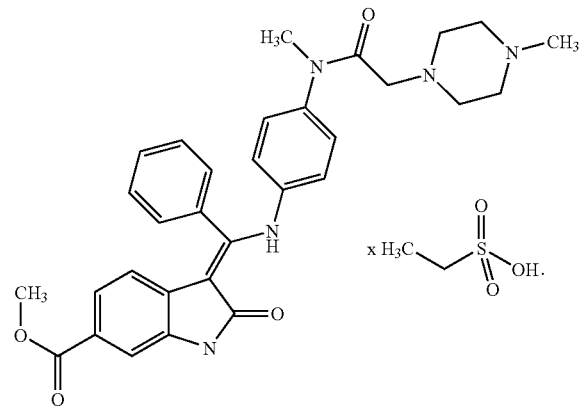

7 Claims, 2 Drawing Sheets

Figure 1: X-ray powder diffractogram of crystalline 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.
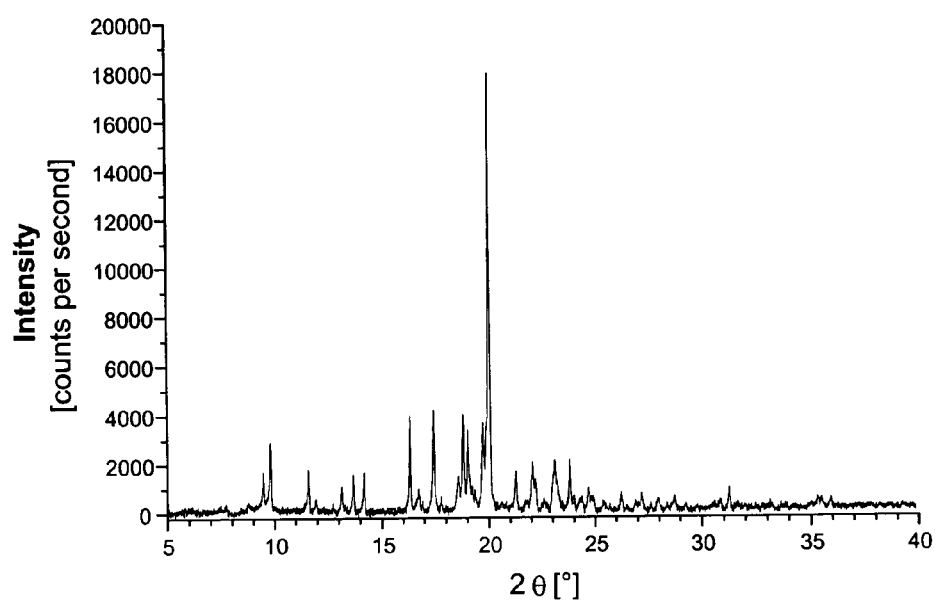

Figure 2: Thermoanalysis and determination of the melting point (DSC) of crystalline 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.
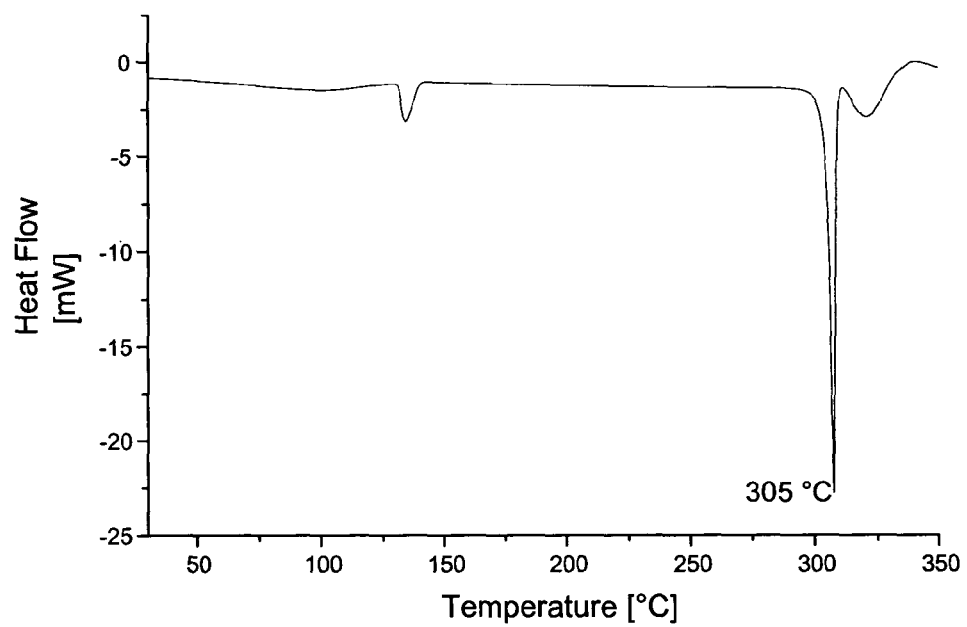

3-Z-[1-(4-(N-((4-METHYL-PIPERAZIN-1-YL)-METHYLCARBONYL)-N-METHYL-AMINO)-ANILINO)-1-PHENYL-METHYLENE]-6-METHOXYCARBONYL-2-INDOLINONE-MONOETHANESULPHONATE AND THE USE THEREOF AS A PHARMACEUTICAL COMPOSITION

RELATED APPLICATIONS

Benefit of U.S. Provisional Application Ser. No. 60/404,460, filed on Aug. 19, 2002 is hereby claimed.

FIELD OF THE INVENTION

The present invention relates to the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate of formula I and the use thereof in a pharmaceutical composition.

Formula I:

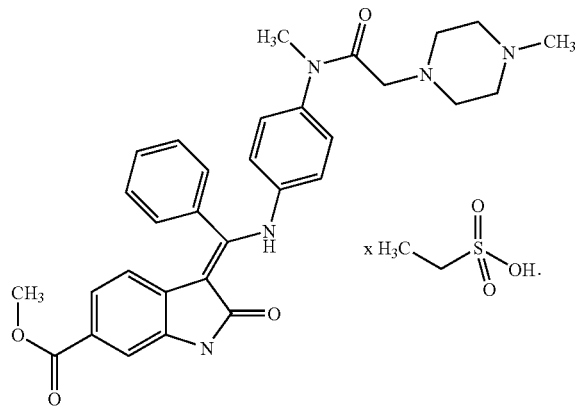

BACKGROUND TO THE INVENTION

A number of 2-indolinone derivatives are already known in the prior art. Thus, for example, International Patent Application WO 01/27081 discloses 2-indolinone derivatives which have valuable pharmacological properties.

Like the 2-indolinone derivatives mentioned in the prior art, the compound of formula I also has, in particular, an inhibiting effect on various kinases, particularly receptor tyrosine kinases such as VEGFR1, VEGFR2, VEGFR3, PDGFRα, PDGFRβ, FGFR1, FGFR3, EGFR, HER2, c-Kit, IGF1R, Flt-3 and HGFR, and on the proliferation of cultivated human cells, particularly endothelial cells, e.g. in angiogenesis, but also on the proliferation of other cells, particularly tumour cells.

The pharmacologically valuable properties of the indolinone derivatives disclosed in the art and mentioned above constitute the basic prerequisite for effective use of the compounds as pharmaceutical compositions. An active substance must in any case satisfy additional requirements in order to be accepted for use as a drug. These parameters are largely connected with the physicochemical nature of the active substance.

Without being restrictive, examples of these parameters are the stability of effect of the starting substance under various environmental conditions, the stability during production of the pharmaceutical formulation and stability in the final compositions of the drug. The pharmaceutically active substance used to prepare the pharmaceutical compositions should therefore have great stability which is ensured even under all kinds of environmental conditions. This is absolutely essential to prevent pharmaceutical compositions being used which contain breakdown products, for example, in addition to the active substance itself. In such a case the content of active substance present in the pharmaceutical formulation might be lower than specified.

The absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. In addition, the uptake of moisture may reduce the content of pharmaceutically active substance during manufacture if the pharmaceutical substance is exposed to the environment without being protected from moisture in any way. Preferably, therefore, a pharmaceutically active substance should be only slightly hygroscopic.

As the crystal modification of an active substance is important to the reproducible active substance content of a preparation, there is a need to clarify as far as possible any existing polymorphism of an active substance present in crystalline form. If there are different polymorphic modifications of an active substance care must be taken to ensure that the crystalline modification of the substance does not change in the pharmaceutical preparation later produced from it. Otherwise, this could have a harmful effect on the reproducible potency of the drug. Against this background, active substances characterised by only slight polymorphism are preferred.

Another criterion which may be of exceptional importance under certain circumstances depending on the choice of formulation or the choice of manufacturing process is the solubility of the active substance. If for example pharmaceutical solutions are prepared (e.g. for infusions) it is essential that the active substance should be sufficiently soluble in physiologically acceptable solvents. It is also very important for drugs which are to be taken orally that the active substance should be sufficiently soluble.

The problem of the present invention is to provide a pharmaceutically active substance which not only is characterised by high pharmacological potency but also satisfies the above-mentioned physicochemical requirements as far as possible.

BRIEF DESCRIPTION OF THE FIGURES

FIG. 1 shows the X-ray powder diffractogram of crystalline 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

FIG. 2 shows the thermoanalysis and determination of the melting point (DSC) of crystalline 3-Z-[1-(4-(N-((4-methyl-piperazin-1-yl)-methylcarbonyl)-N-amino)-anilino)-1-phenyl-methylene]-6-methoxycarbonyl-2-indolinone-monoethanesulphonate.

DETAILED DESCRIPTION OF THE INVENTION

Surprisingly, it has been found that the problem outlined above is solved by the salt 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate of formula I.

The monoethanesulphonate according to the invention is characterised by good crystallinity and low amorphisation during grinding and compression. In addition it is not hygroscopic and is readily soluble in physiologically acceptable solvents.

The crystalline form of the monoethanesulphonate of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone according to the invention is characterised by a melting point of $T_{m.p.}$=305±5° C. (determined by DSC=Differential Scanning Calorimetry; evaluated by the peak maximum; heating rate: 10° C./min). The value given was determined using a DSC 821$^e$ made by Messrs Mettler Toledo.

Therefore a first object of the present invention is the salt 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate, preferably in crystalline form, characterised by a melting point of $T_{m.p.}$=305±5° C. (determined by DSC; evaluation by peak maximum; heating rate: 10° C./min).

The crystalline form of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate according to the invention was investigated in more detail by x-ray powder diffraction. The diagram obtained is shown in FIG. 1.

Table 1 that follows contains the data obtained in this analysis:

TABLE 1

X-ray powder reflections and intensities (standardised) of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

| h | k | l | 2Θ [°] | $d_{hkl}$ Value [Å] | Intensity [%] |
|---|---|---|---|---|---|
| 0 | 0 | 1 | 7.70 | 11.47 | 17.7 |
| 0 | -1 | 0 | 8.78 | 10.07 | 19.2 |
| -1 | 0 | 1 | 9.47 | 9.33 | 26.4 |
| 1 | 0 | 1 | 9.82 | 9.00 | 32.2 |
| 2 | 0 | 0 | 11.59 | 7.63 | 30.9 |
| 0 | -2 | 1 | 11.93 | 7.41 | 26.3 |
| 1 | 2 | 0 | 13.15 | 6.73 | 29.6 |
| -2 | 0 | 1 | 13.69 | 6.47 | 31.8 |
| 2 | 1 | 0 | 14.17 | 6.24 | 30.9 |
| 3 | -1 | 0 | 16.32 | 5.43 | 41.7 |
| 0 | 1 | 2 | 16.72 | 5.30 | 29.0 |
| -1 | 1 | 2 | 16.92 | 5.238 | 9.8 |
| 3 | 0 | 0 | 17.43 | 5.08 | 42.7 |
| 2 | 2 | 0 | 17.77 | 4.99 | 26.9 |
| 1 | -4 | 0 | 18.58 | 4.77 | 31.1 |
| -3 | 0 | 1 | 18.81 | 4.71 | 41.8 |
| -2 | 0 | 2 | 19.03 | 4.66 | 39.2 |
| 3 | -3 | 1 | 19.73 | 4.50 | 40.2 |
| 0 | 4 | 0 | 19.87 | 4.47 | 6.2 |
| 2 | -4 | 1 | 20.03 | 4.43 | 100.0 |
| 0 | -4 | 1 | 20.61 | 4.31 | 8.3 |
| -3 | -1 | 1 | 20.83 | 4.26 | 5.5 |
| 1 | 2 | 2 | 21.26 | 4.18 | 31.1 |
| -1 | 3 | 2 | 21.76 | 4.08 | 19.8 |
| 0 | 4 | 1 | 22.05 | 4.03 | 32.4 |
| 3 | -4 | 1 | 22.19 | 4.00 | 10.1 |
| 0 | 3 | 2 | 22.57 | 3.94 | 25.6 |
| -3 | 4 | 1 | 23.10 | 3.85 | 32.3 |
| -1 | 0 | 3 | 23.81 | 3.73 | 32.0 |
| 1 | 4 | 1 | 24.69 | 3.60 | 26.6 |
| 1 | 3 | 2 | 24.78 | 3.58 | 24.6 |
| 0 | 5 | 0 | 24.91 | 3.572 | 15.6 |
| -1 | 5 | 1 | 25.42 | 3.50 | 23.7 |
| -4 | 4 | 1 | 26.24 | 3.39 | 24.8 |

TABLE 1-continued

X-ray powder reflections and intensities (standardised) of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

| h | k | l | 2Θ [°] | $d_{hkl}$ Value [Å] | Intensity [%] |
|---|---|---|---|---|---|
| 3 | -2 | 2 | 26.91 | 3.31 | 22.9 |
| -3 | 4 | 2 | 27.19 | 3.28 | 23.9 |
| 1 | 5 | 0 | 27.61 | 3.23 | 22.0 |
| -1 | -5 | 1 | 27.95 | 3.19 | 22.3 |
| 3 | -1 | 3 | 28.71 | 3.11 | 22.1 |
| 5 | 0 | 0 | 29.25 | 3.05 | 20.2 |

In Table 1 above the value "2Θ [°]" denotes the angle of diffraction in degrees and the value "$d_{hkl}$ [Å]" denotes the specified distances in Å between the lattice planes.

The x-ray powder diagram was recorded, within the scope of the present invention, using a Bruker D8 Advanced-diffractometer fitted with a location-sensitive detector (OED) and a Cu anode as the x-ray source (CuK$_\alpha$ radiation, λ=1.54056 Å, 40 kV, 40 mA).

According to the findings shown in Table 1 the present invention relates to crystalline 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate, characterised in that in the x-ray powder diagram it has, inter alia, the characteristic values d=5.43 Å, 5.08 Å, 4.71 Å, 4.50 Å and 4.43 Å with an intensity of more than 40%.

Evaluation of the x-ray powder data obtained yields the unit cell of the compound according to the invention, the crystallographic data of which are provided in Table 2 below:

| Formula | $C_{66}H_{78}N_{10}O_{15}S_2$ |
|---|---|
| Molecular weight | 1315.52 |
| Crystal system | triclinic |
| a | 16.332 Å |
| b | 19.199 Å |
| c | 11.503 Å |
| α | 95.27° |
| β | 90.13° |
| γ | 110.83° |
| V | 3354.4 Å$^3$ |

The unit cell is defined by the lengths of the side of this cell a, b and c, by the relative angles α, β and γ of the cell sides to one another and by the cell volume V (see Table 2). Methods of recording and evaluating x-ray powder diagrams for determining unit cells and their dimensions are known in the prior art and are recognised for characterising the crystalline nature and structure of a product.

Thus, the present invention also relates to the crystalline 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate according to the invention, characterised by a unit cell determined by x-ray powder diffractometric measurements, having the following dimensions:

a=16.332 Å
b=19.199 Å
c=11.503 Å
α=95.27°
β=90.13°
γ=110.83°
V=3354.4 Å$^3$

Using a monocrystal it was also possible to determine the space group of the compound according to the invention. The corresponding data are shown in Table 3 below:

| Structural resolution | From monocrystal data |
|---|---|
| Space group | P1 (#2) |
| Density (calculated) | 2.605 g/cm$^3$ |
| Cell contents | 2 molecules of different conformation |
| | 2 × EtSO$_4$ |
| | 1 × H$_2$O |

Under standard conditions the monoethanesulphonate of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate according to the invention is present in the form of the hemihydrate, from which water escapes at a temperature of about 130° C. FIG. 2 shows the thermoanalysis.

The present invention also relates to the metabolites of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate of formula I, to prodrugs of this compound or of these metabolites obtained via, for example, chemical or non-chemical derivatization of the entire molecule or of one or more chemical groups on the molecule, and to the use thereof in a pharmaceutical composition.

Hence, metabolites of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate may occur via, for example, de-esterification of an ester group on the molecule. This de-esterification may occur in-vivo through the action of specific or a-specific esterases present in the body of the patient to which the drug is administered.

Prodrugs of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate or of metabolites thereof may be obtained via, for example, any chemical substitution of a carboxy or amino group present on the molecule or by substitution of the the N-1-atom of the indolinone moiety by a group which may be cleaved in vivo.

By a group which may be cleaved in vivo and converted in-vivo into a carboxy group is meant for example a hydroxymethyl group, a carboxy group esterified with an alcohol wherein the alcoholic moiety preferably denotes a $C_{1-6}$-alkanol, a phenyl-$C_{1-3}$-alkanol, a $C_{3-9}$-cycloalkanol, while a $C_{5-8}$-cycloalkanol may additionally be substituted by one or two $C_{1-3}$-alkyl groups, a $C_{5-8}$-cycloalkanol, wherein a methylene group is replaced in the 3 or 4 position by an oxygen atom or by an imino group optionally substituted by a $C_{1-3}$-alkyl, phenyl-$C_{1-3}$-alkyl, phenyl-$C_{1-3}$-alkoxy-carbonyl or $C_{1-6}$-alkyl-carbonyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which carries a double or triple bond, a $C_{3-8}$-cycloalkyl-$C_{1-3}$-alkanol, a bicycloalkanol with a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of formula $R_a$—CO—O—($R_b$C$R_c$)—OH, wherein $R_a$ denotes a $C_{1-8}$-alkyl, $C_{5-7}$-cycloalkyl, phenyl or phenyl-$C_{1-3}$-alkyl group, $R_b$ denotes a hydrogen atom, a $C_{1-3}$-alkyl, $C_{5-7}$-cycloalkyl or phenyl group and $R_c$ denotes a hydrogen atom or a $C_{1-3}$-alkyl group, and by a group which may be cleaved in vivo from an amino group or from the N-1 atom of the indolinone moiety is meant for example a hydroxy group, an acyl group such as the benzoyl or pyridinoyl group or a $C_{1-16}$-alkyl-carbonyl group such as the formyl, acetyl, propionyl, butanoyl, pentanoyl or hexanoyl group, an allyloxycarbonyl group, a $C_{1-16}$-alkoxy-carbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxy-carbonyl group such as the benzyloxycarbonyl, phenylethoxycarbonyl or phenylpropoxycarbonyl group, a $C_{1-3}$-alkylsulphonyl-$C_{1-4}$-alkoxy-carbonyl, $C_{1-3}$-alkoxy-$C_{2-4}$-alkoxy-$C_{2-4}$-alkoxy-carbonyl or $R_a$CO—O—($R_b$C$R_c$)—O—CO-group wherein $R_a$ denotes a $C_{1-8}$-alkyl, $C_{5-7}$-cycloalkyl, phenyl or phenyl-$C_{1-3}$-alkyl group, $R_b$ denotes a hydrogen atom, a $C_{1-3}$-alkyl, $C_{5-7}$-cycloalkyl or phenyl group and $R_c$ denotes a hydrogen atom, a $C_{1-3}$-alkyl or $R_a$CO—O—($R_b$C$R_c$)—O-group wherein $R_a$ to $R_c$ are as hereinbefore defined, and additionally the phthalimido group, while the above-mentioned ester groups may also be used as a group which can be converted in vivo into a carboxy group.

Preferred prodrug groups for a carboxy group include a $C_{1-6}$-alkoxy-carbonyl group such as the methoxycarbonyl, ethoxycarbonyl, n-propyloxycarbonyl, isopropyloxycarbonyl, n-butyloxy-carbonyl, n-pentyloxycarbonyl, n-hexyloxycarbonyl or cyclohexyloxycarbonyl group or phenyl-$C_{1-3}$-alkoxy-carbonyl group such as the benzyloxycarbonyl group and for an amino group or the N-1 group of the indolinone moiety a $C_{1-9}$-alkoxy-carbonyl group such as the methoxycarbonyl, ethoxycarbonyl, n-propyloxycarbonyl, isopropyloxycarbonyl, n-butyloxycarbonyl, n-pentyloxycarbonyl, n-hexyloxycarbonyl, cyclohexyloxycarbonyl, n-heptyloxycarbonyl, n-octyloxycarbonyl or n-nonyloxycarbonyl group, a phenyl-$C_{1-3}$-alkoxy-carbonyl group such as the benzyloxycarbonyl group, a phenylcarbonyl group optionally substituted by a $C_{1-3}$-alkyl group such as the benzoyl or 4-ethyl-benzoyl group, a pyridinoyl group such as the nicotinoyl group, a $C_{1-3}$-alkylsulphonyl-n-$C_{2-3}$-alkoxy-carbonyl or $C_{1-3}$-alkoxy-$C_{2-3}$-alkoxy-$C_{1-4}$alkoxy-carbonyl group such as the 2-methylsulphonylethoxycarbonyl or 2-(2-ethoxy)-ethoxycarbonyl group.

Moreover, the saturated alkyl and alkoxy moieties containing more than 2 carbon atoms mentioned in the definitions above as well as the alkanoyl and unsaturated alkyl moieties which contain more than 3 carbon atoms also include the branched isomers thereof such as the isopropyl, tert.butyl, isobutyl group, etc.

For the chemical synthesis of the above-mentioned metabolites and prodrugs, reference is made to WO 01/27081.

Experimental studies have shown that a metabolite of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate is the de-esterified 3-Z-[1-(4-(N-((4-methyl-piperazin-1-yl)-carbonyl)-N-methyl-amino)-anilino)-1-phenyl-methylene]-6-carbonyl-2-indolinone. The in-vitro inhibitory activity of this metabolite on several kinases has been evaluated, using standard known kinase inhibition assays as well as a standard known cellular proliferation inhibition assay (inhibition of the proliferation of Human Umbilical Cord Endothelial Cells stimulated by the VEGF, the so-called "HUVEC cellular assay"). These experimental results have shown that this metabolite inhibits several kinases, such as VEGFR-2, VEGFR-3, Her-2, FGFR-1, PDGFR-alpha or InsR, as well as the proliferation of HUVEC VEGF stimulated cells.

Furthermore, the compounds in accordance with the present invention may be administered to a patient in need thereof in any type of galenical form such as tablets, capsules or in a liquid formulation.

An especially suitable pharmaceutical formulation for the compounds in accordance with the present invention is soft gelatine capsules. Suitable soft gelatine capsules for the encapsulation of pharmaceutical compounds and the process for their preparation are described, for example, in GB patent No. 395546, U.S. Pat. No. 2,720,463, U.S. Pat. No. 2,870,062, U.S. Pat. No. 4,829,057, and in the following publications: ANON (Verpack-Rundsch., Vol. 21, No. 1, January 1970, pp. 136–138), Lachman et al. (The Theory and Practice of Industrial Pharmacy, Chap. 13, published by Lea & Febiger, 1970), Ebert (Soft Gelatine Capsules: A Unique Dosage Form, reprint from Pharmaceutical Technology, October 1977) and R. F. Jimerson (Soft Gelatine Capsule Update, Drug Development and Industrial Pharmacy, Vol. 12 (8 & 9), pp. 1133–1144, 1986).

EXPERIMENTAL SECTION

The HPLC data given below were measured using the parameters listed hereinafter:

Column: Inertsil ODS-2, 5 μm, 53×4.0 mm; solvent A: 0.2% aqueous $KH_2PO_4$ solution, adjusted to pH=6.0 with dilute sodium hydroxide solution; solvent B: acetonitrile; column temperature: 45° C.; flow: 1 mL/min; gradient system: within 5 minutes, from 5% to 30% solvent B, then maintained for 1 minute at 30% solvent B and then within 9 minutes increased to 55% solvent B, then maintained for 4 minutes at 55% B; concentration of the sample solution: 5 mg/mL in acetonitrile/water=3:7; injection volume: 3 μL; detection at 225 nm and 210 nm, respectively.

EXAMPLE 1

3-Z-[1-(4-(N-((4-methyl-piperazin-1-yl)-methylcarbonyl)-N-methyl-amino)-anilino)-1-phenyl-methylene]-6-methoxycarbonyl-2-indolinone 10.5 g (30.0 mmol) of 1-acetyl-3-(1-ethoxy-1-phenylmethylene)-6-methoxycarbonyl-2-indolinone (for preparation see WO 01/27081 mentioned above) and 8.60 g (33.0 mmol) N-[(4-methyl-piperazin-1-yl)-methylcarbonyl]-N-methyl-p-phenylenediamine (for preparation see WO 01/27081 mentioned above) are dissolved in 80 mL of dimethylformamide and stirred for 1 hour at 80° C. After cooling 6.50 mL of piperidine are added and the mixture is stirred for another two hours at ambient temperature. Water is added, the precipitate formed is suction filtered and washed with a little water. The residue is suspended in 200 mL of methanol, suction filtered and washed with cold water and diethyl ether. The substance is dried in vacuo at 110° C.

| Yield: | 12.4 g (77% of theory), |
| --- | --- |
| IR spectrum: | 1610, 1655, 1711 $cm^1$ |
| $T_{m.p.}$ = | 253° C. |
| Empirical formula: | $C_{31}H_{33}N_5O_4$ |
| ESI mass spectrum: | m/z = 540 $[M + H]^+$ |
| Elemental analysis: | calculated: C 68.99 H 6.16 N 12.98 |
| | found: C 68.32 H 6.29 N 12.85 |

EXAMPLE 2

3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate 605 g (1.12 mol) of 3-Z-[1-(4-(N-((4-methyl-piperazin-1-yl)-methylcarbonyl)-N-methyl-amino)-anilino)-1-phenyl-methylene]-6-methoxycarbonyl-2-indolinone are suspended in 9 liters of methanol and heated to 50° C. 183.7 g (1.121 mol) of 70% aqueous ethanesulphonic acid are added. The solution obtained is cooled to 40° C. and 4.5 liters of tert.-butylmethylether are added. After a few minutes crystallisation sets in. To achieve total precipitation the mixture is stirred for another 16 hours at ambient temperature. After cooling to 10° C. it is suction filtered, washed with 2 liters of tert.-butylmethylether and dried at 40° C. in vacuo.

| Yield: | 638 g (87.6% of theory) |
| --- | --- |
| $T_{m.p.}$ = | 305 ± 5° C. (DSC 10 K/min) |
| Purity according to HPLC: | 99.4% |
| Water content: | 1.0 to 2.0% (KF) |

What is claimed is:

1. 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

2. 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate hemihydrate in crystalline form, having a melting point of $T_{m.p.}$=305±5° C. (determined by DSC; evaluation using peak-maximum; heating rate: 10° C./min).

3. Crystalline 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate hemihydrate according to claim 2, the X-ray powder diagram of which includes, inter alia, the characteristic values d=5.43 Å, 5.08 Å, 4.71 Å, 4.50 Å and 4.43 Å with an intensity of more than 40%.

4. Crystalline 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate hemihydrate according to claim 2, characterised by a unit cell determined by X-ray powder diffractometric measurements having the following dimensions:

a=16.332 Å,
b=19.199 Å,
c=11.503 Å,
α=95.27°,
β=90.13°,
γ=110.83° and
V=3354.4 $Å^3$.

5. A pharmaceutical composition comprising 3-Z-[1-(4-(N-((4-methyl-piperazin-1-yl)-methylcarbonyl)-N-methyl-amino)-anilino)-1-phenyl-methylene]-6-methoxycarbonyl- 2-indolinone-monoethanesulphonate and one or more inert carriers and/or diluents.

6. A prodrug of 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

7. 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate hemihydrate in crystalline form.

* * * * *